United States Patent [19]

Vurek et al.

[11] Patent Number: 5,551,300

[45] Date of Patent: Sep. 3, 1996

[54] USER-RESTRICTED PASSAGE IN REUSABLE PORTION OF DEVICE FOR MONITORING A PHYSIOLOGICAL PRESSURE

[75] Inventors: Gerald G. Vurek, Mountain View; Harlow B. Christianson, San Jose, both of Calif.

[73] Assignee: Abbott Laboratories, Abbott Park, Ill.

[21] Appl. No.: 574,206

[22] Filed: Dec. 18, 1995

[51] Int. Cl.⁶ .................................. G01L 7/00; A61B 5/02
[52] U.S. Cl. .............................. 73/706; 73/756; 128/673; 128/748
[58] Field of Search ........................... 73/706, 756, 715, 73/716, 717, 723; 128/672, 673, 675, 748

[56] References Cited

U.S. PATENT DOCUMENTS

| | | | |
|---|---|---|---|
| 3,720,201 | 3/1973 | Ramsey, III | 128/2.05 D |
| 3,890,842 | 6/1975 | Ramsey, III | 73/420 |
| 4,185,641 | 1/1980 | Minior et al. | 128/675 |
| 4,227,420 | 10/1980 | Lamadrid | 73/706 X |
| 4,252,126 | 2/1981 | Mandl | 128/673 |
| 4,576,181 | 3/1986 | Wallace et al. | 128/675 |
| 4,611,601 | 9/1986 | Bowman | 128/673 |
| 4,672,974 | 6/1987 | Lee | 128/673 |
| 4,686,764 | 8/1987 | Adams et al. | 29/592 |
| 4,856,340 | 8/1989 | Garrison | 73/715 |
| 4,920,972 | 5/1990 | Frank et al. | 128/675 |
| 4,934,375 | 6/1990 | Cole et al. | 128/673 |
| 4,994,035 | 2/1991 | Mokros | 604/118 |
| 5,018,529 | 5/1991 | Tenerz et al. | 128/667 |
| 5,048,531 | 9/1991 | Spotts et al. | 128/675 |
| 5,086,777 | 2/1992 | Hishii | 128/675 |
| 5,105,820 | 4/1992 | Moriuchi et al. | 128/675 |
| 5,135,002 | 8/1992 | Kirchner et al. | 128/673 |
| 5,207,102 | 5/1993 | Takahashi et al. | 73/727 |
| 5,237,999 | 8/1993 | von Berg | 128/673 |
| 5,275,169 | 1/1994 | Afromowitz et al. | 128/673 |

*Primary Examiner*—Richard Chilcot
*Assistant Examiner*—Joseph L. Felber
*Attorney, Agent, or Firm*—Ronald M. Anderson

[57] ABSTRACT

A pressure monitoring apparatus for use in monitoring a physiological fluid pressure in successive patients. Three embodiments of the pressure monitoring apparatus (10, 100, 200) are disclosed, each of which include a disposable portion (12, 12', 12") and a reusable portion (14, 14', 14"). Fluid flows through the disposable portion and into a cavity (48) that is covered with an elastomeric membrane (46, 46'). When the disposable portion is engaged with the reusable portion, the elastomeric membrane is in contact with a corresponding elastomeric membrane (50, 50'), which covers a pressure sensing cavity (52). A pressure transducer (56) is mounted in the pressure sensing cavity, and the pressure sensing cavity is filled with a fluid and is in fluid communication with a reservoir (38) when not engaged with the disposable portion. When the disposable portion is brought into engagement with the reusable portion, a passage (54, 53) connecting the reservoir with the pressure sensing cavity is blocked, thereby minimizing the volume of fluid within the pressure sensing cavity. In this way, the compliance of the pressure sensing portion is reduced, so that its frequency response is increased. In one embodiment of the pressure monitoring apparatus (100), a slider (110) is provided for covering the elastomeric membrane used on the disposable portion so that exposure of the elastomeric membrane to a fluid pressurized to a level in excess of the rated pressure for the membrane does not damage the membrane.

17 Claims, 7 Drawing Sheets

USER-RESTRICTED PASSAGE IN REUSABLE PORTION OF DEVICE FOR MONITORING A PHYSIOLOGICAL PRESSURE

FIELD OF THE INVENTION

The present invention generally relates to a method and a device for monitoring fluid pressure in a patient's body, and more specifically, to a method and device having a reusable portion that includes a pressure transducer, and a disposable portion that is adapted to be in fluid communication with a patient's physiological fluids, each portion including diaphragms that contact each other for transmitting fluid pressure to the pressure transducer.

BACKGROUND OF THE INVENTION

Electronic pressure transducers are commonly used by medical personnel to monitor blood pressure in the cardiovascular system and the pressure of other physiological fluids. Such devices are typically discarded after being used with a single patient, thereby avoiding any risk of cross contamination of patients. Although the cost of the pressure transducer package that is used in disposable devices of this type is relatively low, it is the most significant portion of the overall cost. Accordingly, it is desirable to substantially reduce the cost of such devices by isolating the pressure transducer from contact with the physiological fluids of a patient so that the pressure transducer portion of the device can be reused with other patients without risk of cross contamination.

U.S. Pat. No. 4,920,972 discloses a reusable pressure transducer that is used in connection with a disposable portion for monitoring blood pressure through a fluid line in which a saline solution or other medicinal fluid flows into a patient's cardiovascular system. The disposable portion has a dome that covers a cavity. When monitoring cardiovascular pressure, an input port to the cavity in the disposable portion is coupled to a source of the medicinal fluid, and an output port of the disposable portion is coupled through the line to a patient's blood vessel. The cavity is covered with a rubber diaphragm that is sealed around the periphery of the cavity. Pressure in the medicinal fluid flowing through the disposable portion is indicative of the blood pressure in the patient's blood vessel and is applied to the rubber diaphragm covering the cavity.

The reusable portion includes a similarly sized cavity, also covered with a rubber diaphragm, which is in fluid communication with a pressure transducer mounted in the body of the reusable portion. This patent discloses both an earlier embodiment, in which the cavity in the reusable portion is filled with an oil, and an improved embodiment in which the cavity in the reusable portion is filled with a gel. A slight distention of the rubber diaphragm in the reusable portion occurs as the gel, which is formed in place from an injected liquid, cures. The slightly distended robber diaphragm of the reusable portion thus has a "good fit" with the diaphragm of the disposable portion, when the disposable portion and reusable portion are coupled together with their respective rubber diaphragms in contact. Pressure exerted by the rubber diaphragm in the disposable portion against the rubber diaphragm of the reusable portion is transmitted through the gel (or oil) to the pressure transducer.

In U.S. Pat. No. 3,720,201, a disposable body fluid pressure monitor is disclosed that includes a tube coupled in fluid communication with a patient's body fluid. A diaphragm within the tube separates the body fluid from a cavity that is in fluid communication with a pressure sensing aneroid manometer or other standard pressure sensor. The tube is discarded after being used with a patient, but the pressure sensing device is reused, since it is protected from contamination by the diaphragm. A similar arrangement is disclosed in U.S. Pat. No. 3,890,842.

Although the pressure monitoring device disclosed in the above noted U.S. Pat. No. 4,920,972 has several clear advantages over other prior art reusable pressure monitoring devices, it does not achieve a desired high frequency response. The volume of gel (or oil) within the cavity of the reusable portion of this prior art device tends to impose an upper limit on the frequency response by providing additional compliance to the device.

Ideally, a physician will want to observe certain aspects of blood pressure that can only be determined with a higher frequency response than is provided by the prior art device discussed above. For example, assuming that the line coupling the disposable portion of the pressure monitoring device to the patient's blood stream is about 72 inches in length, the pressure monitoring device should have a maximum frequency response of at least 20 Hz. With an upper frequency response at this level, the pressure monitoring device will enable a physician to observe the dichrotic notch in the signal produced by the pressure transducer. The dichrotic notch in the blood pressure signal corresponds to the opening and closing of the aortic valve in the patient's heart. By observing the dichrotic notch, a physician can evaluate the quality of the patient's heart beat and the quality of the systolic and diastolic pressure measurements. A sufficiently high frequency response also enables medical personnel to detect the presence of bubbles in the fluid line, between the patient's blood vessel and the disposable portion of the pressure monitoring device.

The volume of fluid (including a gel) that couples the diaphragm of the reusable portion of the pressure monitor to the pressure transducer affects the compliance of the reusable portion, which directly affects the frequency response of the pressure monitor. Due to variations in the volume of fluid in the cavity below the diaphragm of the reusable portion caused by temperature, it is not sufficient to simply provide a small closed cavity. Instead, it is preferable to provide for variations in the volume of this fluid, for example, by incorporating a reservoir for the fluid in the reusable portion. However, the added volume of fluid in a reservoir and its compliance can decrease the maximum frequency response of the pressure monitoring device. The prior art does not address this problem.

SUMMARY OF THE INVENTION

In accordance with the present invention, a pressure monitor is defined for monitoring fluid pressure in a line that is in fluid communication with a physiological fluid. The pressure monitor comprises a disposable portion that includes a first housing. In addition, the disposable portion includes a port adapted to couple to the line, a first cavity disposed in the first housing, in fluid communication with the port, and a first elastomeric membrane that sealingly covers the first cavity. A reusable portion is provided that includes a second housing adapted to engage the first housing. The reusable portion comprises a second cavity disposed in the second housing, a second elastomeric membrane covering the second cavity and disposed to contact the first elastomeric membrane when the first housing is engaged with the second housing. A reservoir is disposed in the second housing and is in fluid communication with the second cavity via a passage that connects the reservoir to the second cavity when the second housing is not engaged with the first housing. The reservoir, passage, and second cavity are filled with a substantially nonvolatile fluid. A pressure transducer is disposed adjacent to the second cavity, and is used for producing a signal indicative of the pressure of the fluid in the line when the first housing and second housing are engaged. Engagement of the first housing with the second housing interrupts the fluid communication through the passage between the reservoir and the second cavity to minimize the volume of the nonvolatile fluid that transmits pressure from the second membrane to the pressure transducer. Consequently, a characteristic maximum frequency response of the pressure monitor is substantially higher than it would be if the fluid communication through the passage were not interrupted.

The second elastomeric membrane preferably defines one side of the passage. Fluid pressure causes the second elastomeric membrane to be distended away from an underlying surface of the second housing to enable the nonvolatile fluid to flow between the second elastomeric membrane and the underlying surface of the second housing, providing fluid communication between the reservoir and the second cavity. In one embodiment of the invention, a surface of the first housing that abuts against a corresponding surface of the second housing includes a ridge that extends outwardly to force the second elastomeric membrane into the passage. This action interrupts fluid communication between the reservoir and the second cavity by forcing the second elastomeric membrane into the passage when the first housing is engaged with the second housing. This embodiment of the disposable portion is separately defined by the claims.

In another embodiment, the pressure monitor further comprises a valve that interrupts fluid communication between the reservoir and the second cavity when the first housing is engaged with the second housing.

In the preferred form of the pressure monitor, the nonvolatile fluid is at a pressure in excess of ambient air pressure, thereby causing the second elastomeric membrane to distend outwardly. Outward distention of the second elastomeric membrane ensures a substantially full contact between the second elastomeric membrane and the first elastomeric membrane, over the second cavity and the first cavity.

In one embodiment, at least one arm extends from either the first or second housing and has a tang to engage the other of the first and the second housing. The arm and tang cooperate to maintain the first housing in contact with the second housing when fluid pressure in the line is being monitored.

Yet another embodiment of the pressure monitor further comprises a cover for the first elastomeric membrane, to cover the first cavity when the first housing is not engaged with the second housing and to prevent a potentially damaging distention of the first elastomeric membrane that might be caused by an excessive fluid pressure in the first cavity. The cover preferably comprises a slide that is movable between a first position in which the slide covers the first elastomeric membrane, and a second position in which the slide engages the second housing to couple the first housing against the second housing, with the first elastomeric membrane in contact with the second elastomeric membrane.

A further aspect of the present invention is directed to a method for monitoring a physiological fluid pressure. The method enables a pressure transducer that is employed to monitor the fluid pressure to be used with other patients without cross contamination. The steps of the method relate to functions that are generally equivalent to those implemented by the elements comprising the pressure monitor described above.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein.

Figure 9:
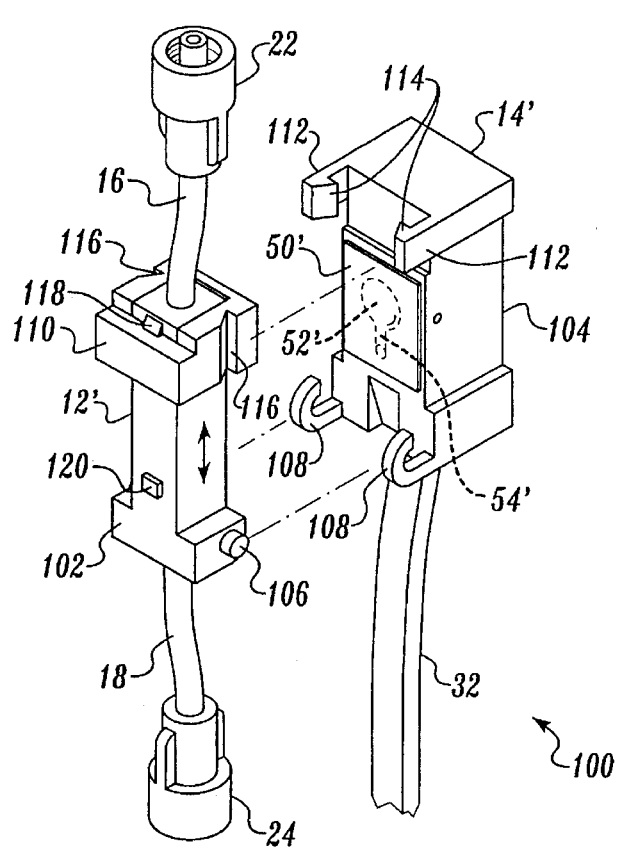
FIG. 9 is an isometric view showing a second embodiment of the pressure monitoring apparatus, with the reusable portion separate from the disposable portion.
Figure 11:
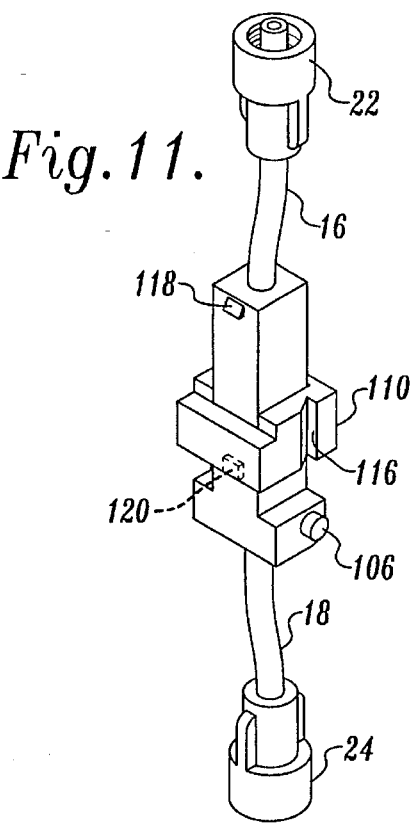
Figure 12:
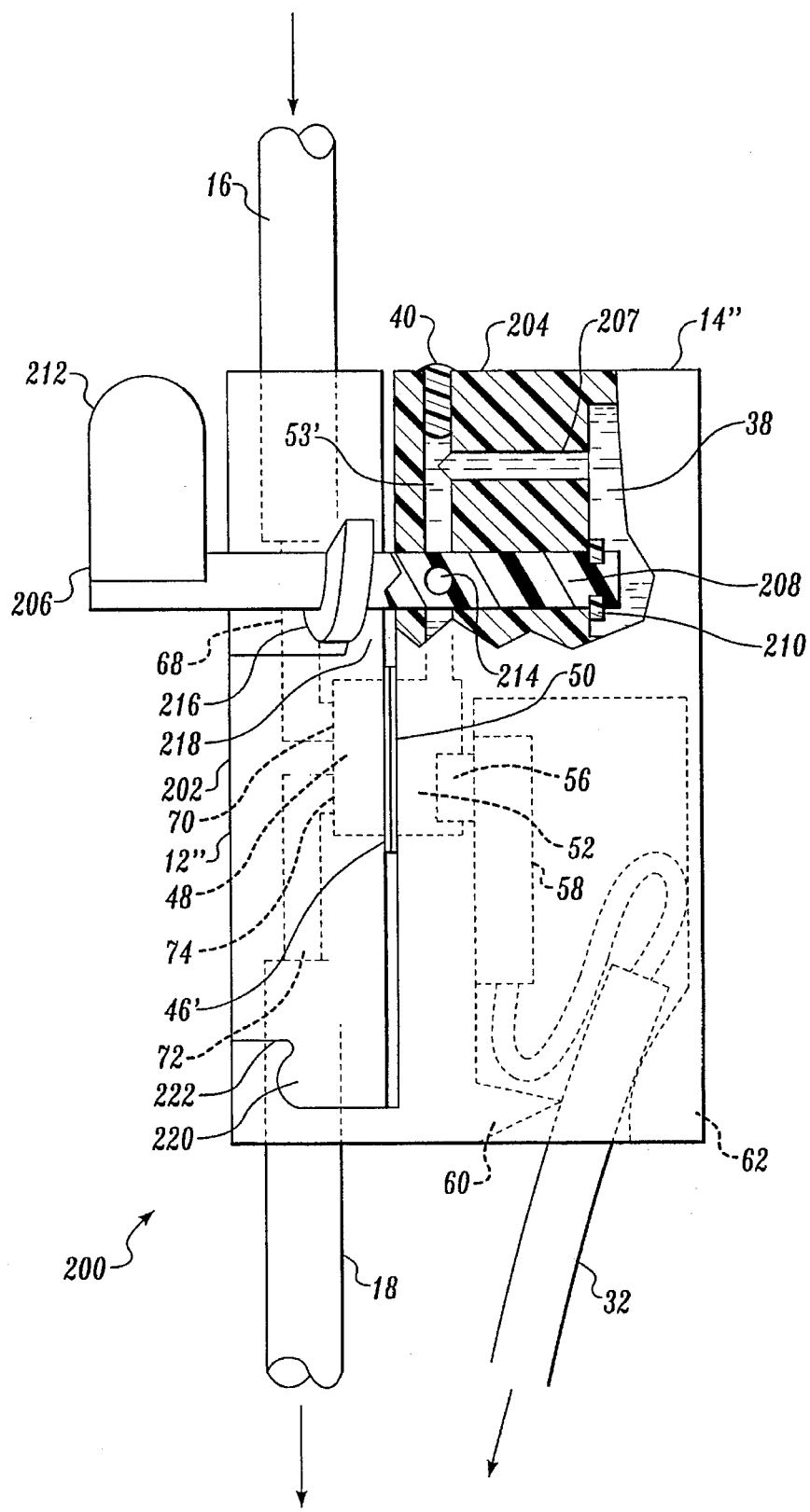

FIG. 11 is an isometric view of the disposable portion of the pressure monitoring apparatus of FIG. 9, showing a back surface of the disposable portion and illustrating the slider in a position to cover an elastomeric diaphragm on the disposable portion, to prevent over distention; and FIG. 12 is a partially cut-away side elevational view of a third embodiment of the pressure monitoring apparatus, the cut-away section showing a reservoir, a fluid passage, and a valve that controls fluid communication between the reservoir and a cavity through the passage.

DESCRIPTION OF THE PREFERRED EMBODIMENT

Figure 1:
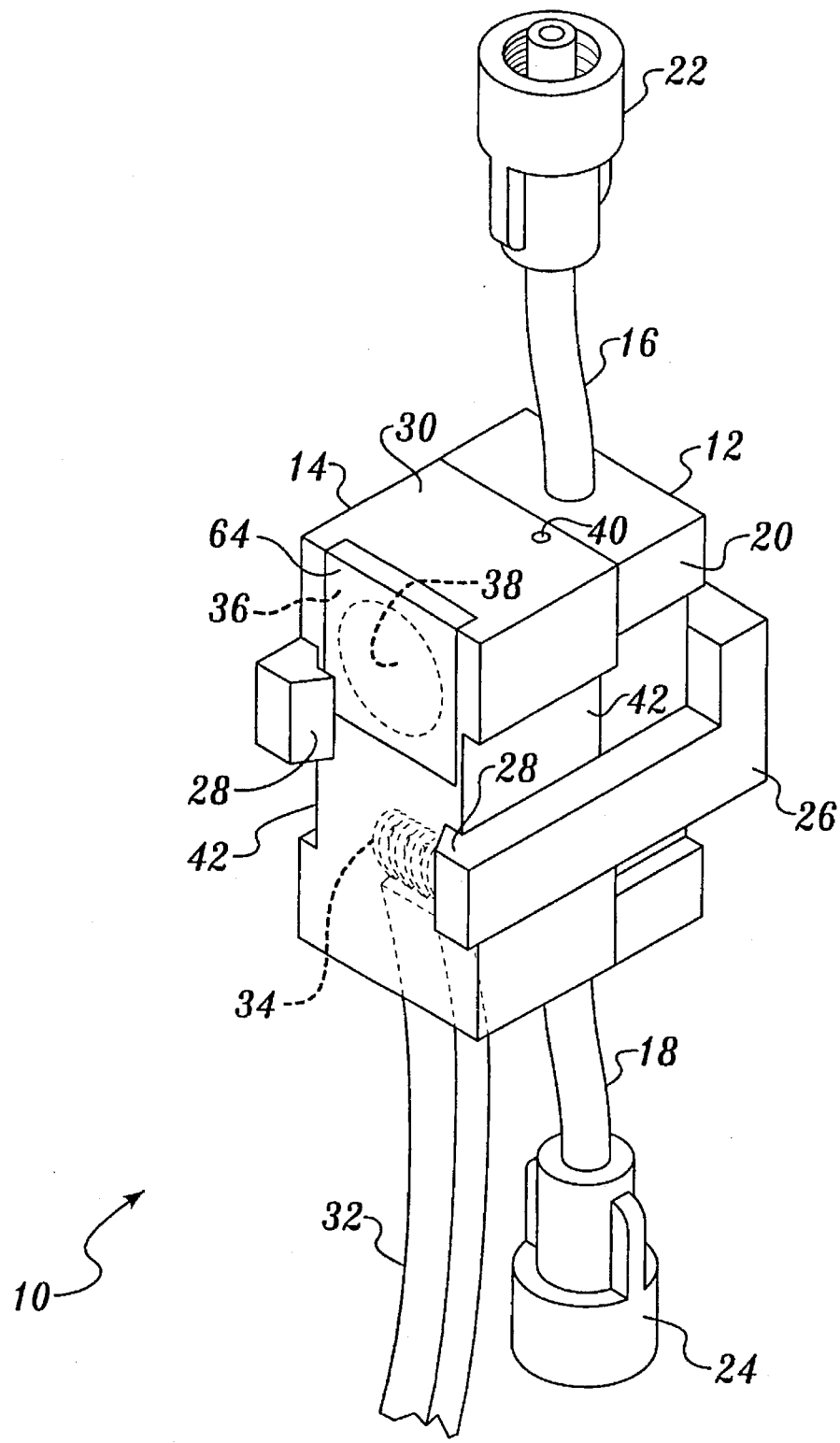
FIG. 1 is an isometric view of a first embodiment of a pressure monitoring apparatus that includes a disposable portion and a reusable portion.
Figure 2:
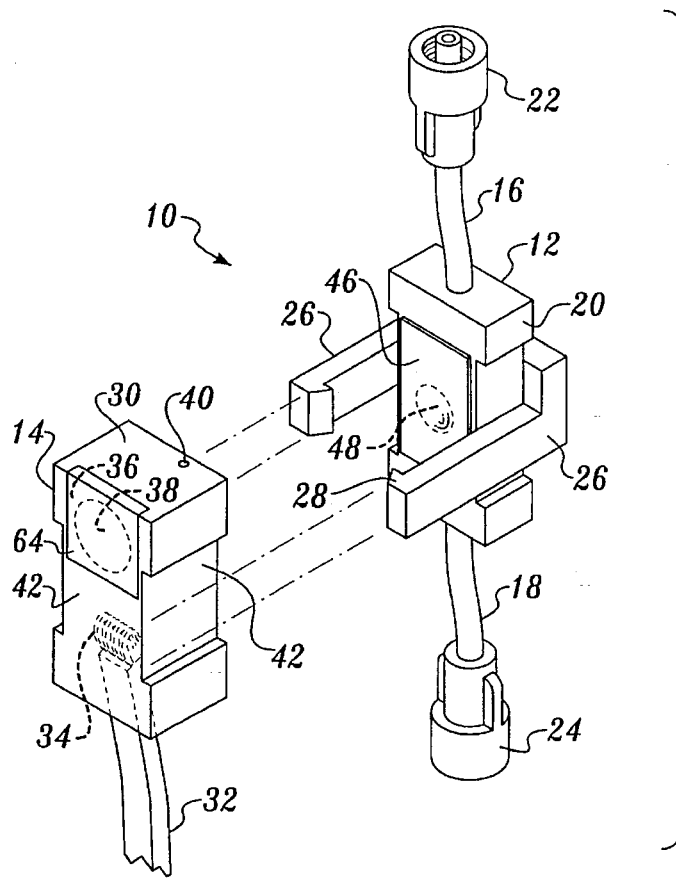
FIG. 2 is an isometric view showing the disposable portion of the first embodiment of the pressure monitoring apparatus separated from the reusable portion.
Figure 3:
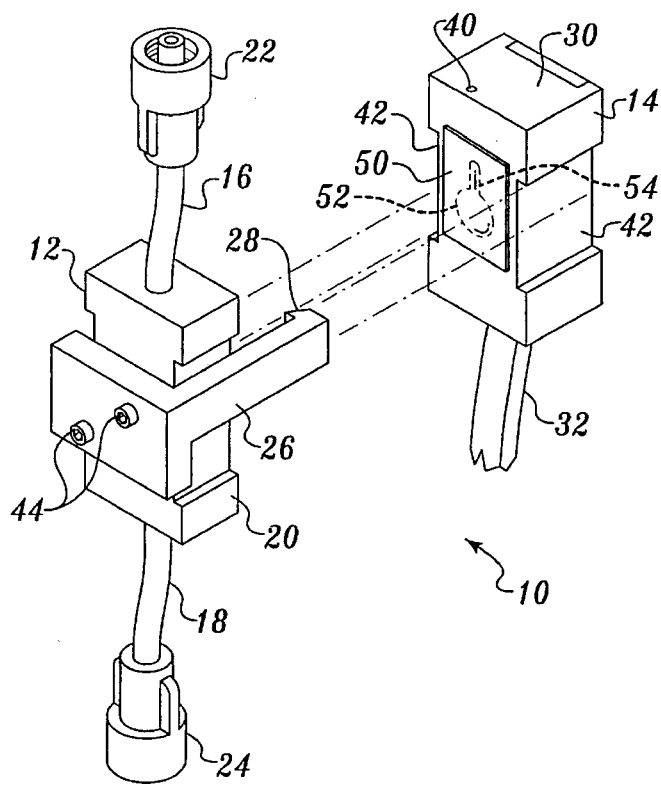
FIG. 3 is an isometric view like that of FIG. 2, but from an opposite side of the pressure monitoring apparatus.

With reference to FIGS. 1 through 3, a first embodiment of pressure monitoring apparatus 10 is shown. Pressure monitoring apparatus 10 includes a disposable portion 12 and a reusable portion 14. In the view shown in FIG. 1, the disposable portion is mechanically coupled to or engaged with the reusable portion so that the pressure of a physiological fluid in the body of a medical patient can be monitored. The pressure of the physiological fluid, which is most commonly blood, is measured indirectly through a medicinal fluid (e.g., a saline solution) that is infused into the patient's body, in fluid communication with the physiological fluid. Since this medicinal fluid is delivered through a line (not shown) that couples the disposable portion of the pressure monitoring apparatus to the cardiovascular (or other) system of the patient, the pressure of the physiological fluid in the patient can thus be monitored by sensing the pressure of the medicinal fluid. The medicinal fluid flows through an inlet port 16 into disposable portion 12, and continues on to the patient through an outlet port 18. Intermediate inlet port 16 and outlet port 18 is a disposable housing 20 having internal passages (not shown in FIG. 1) through which the medicinal fluid flows. A male Luer fitting 22 is connected to inlet port 16, and a similar male Luer fitting 24 is connected to outlet port 18, adapting disposable portion 12 to be connected to a source or the medicinal fluid (not shown) and to the line conveying the medicinal fluid to the patient.

Disposable portion 12 is coupled to or engaged with reusable portion 14 by retaining clip arms 26. Retaining clip arms 26 includes two generally parallel tangs 28 that are offset from each other and are sized to engage the back surface of reusable portion 14, thereby clamping and holding the disposable portion against the reusable portion of the pressure monitoring apparatus.

The reusable portion of the pressure monitoring apparatus thus comprises a reusable housing 30 that is configured to be coupled with the disposable portion to facilitate monitoring the pressure of the medicinal fluid flowing through inlet port 16 and outlet port 18, and thus the pressure of the physiological fluid into which the medicinal fluid flows. The back surface of reusable housing 30 includes an elastomeric cover 36, which is adhesively bonded to the surface of the reusable housing in the area outside the perimeter of a generally cylindrical reservoir 38. Reservoir 38 is formed within the reusable housing. At each side of the reusable housing are notches 42 that accommodate tangs 28 and determine the relative position of the reusable portion and disposable portion by indexing one to the other. On one end of reusable housing 30 is disposed a plug 40, which is used to close off a passage for injecting fluid under pressure into reservoir 38. The purpose of this fluid is disclosed below.

In FIG. 2, an elastomeric diaphragm 46 is shown disposed on an inner face or surface of disposable housing 20. Elastomeric diaphragm 46 is adhesively bonded to the inner surface of the disposable housing outside the periphery of a cavity 48.

In FIG. 3, the inner surface of reusable housing 30 is shown. An elastomeric membrane 50 covers a pressure sensing cavity 52. The elastomeric membrane is adhesively secured to the front surface of disposable housing 30 around the periphery of pressure sensing cavity 52, except along a fluid pressure equalization passage 54. The outline of pressure sensing cavity 52 and pressure equalization passage 54 are shown in dash lines, to indicate that they are covered by elastomeric membrane 50 in the view shown in FIG. 3. This view also discloses two threaded fasteners 44, which are used to secure retaining clip arms 26 to the back of disposable housing 20.

Figure 4:
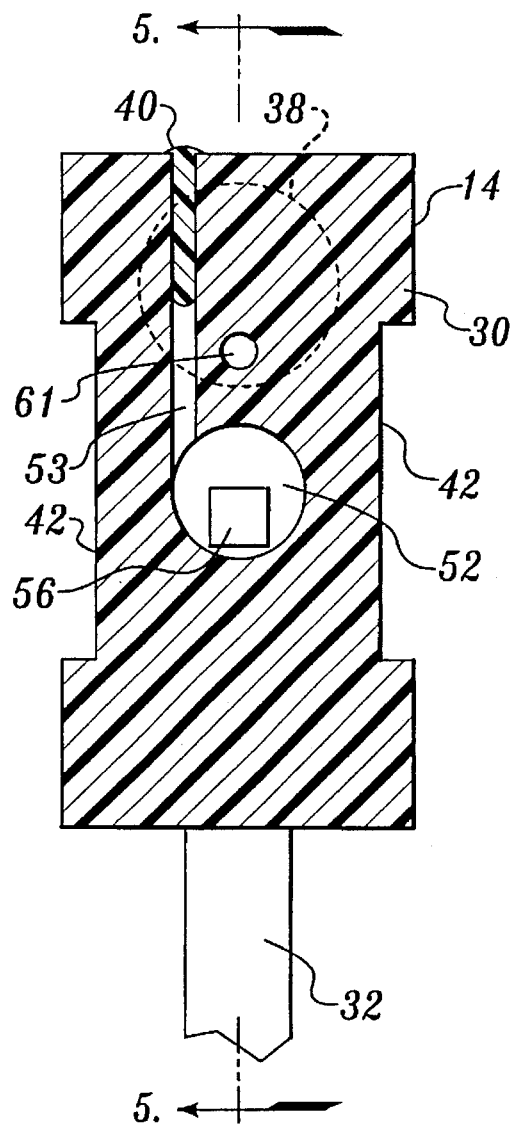
FIG. 4 is a cross-sectional view of the reusable portion of the first embodiment, along section line 4—4 in FIG. 5.

FIGS. 4–7 disclose further details of pressure monitoring apparatus 10. The cross-sectional views of FIGS. 4 and 5 more clearly disclose the interior of reusable housing 30. In FIG. 4, plug 40 is shown in cross section within a fluid injection passage 53. It is through this passage that fluid is injected into pressure sensing cavity 52. Reservoir 38 and pressure sensing cavity 52 are filled with the fluid through fluid injection passage 53. Plug 40 closes and seals fluid injection passage 53, so that the pressure of the fluid in the reservoir is approximately 10 millimeters of mercury (gauge). The fluid is injected through the fluid injection passage into pressure sensing cavity 52 and flows back into reservoir 38 through fluid pressure equalization passage 54, which is formed between the underlying surface of elastomeric membrane 50 and the adjacent surface of reusable housing 30. In an area 66, which is outside the periphery of pressure sensing cavity 52 and which defines the extent of fluid pressure equalization passage 54, elastomeric membrane 50 is adhesively joined and sealed to the underlying surface of reusable housing 30.

Fluid communication is provided between pressure equalization passage 54 and reservoir 38 through a transverse passage 61. Elastomeric cover 36 is adhesively and sealingly secured around the periphery of reservoir 38, thereby preventing the fluid in the reservoir from escaping, and is protected by a cover plate 64. Since the fluid is at a pressure in excess or ambient, elastomeric cover 36 is slightly distended, as is elastomeric membrane 50 (as shown in FIG. 5).

In the preferred embodiment, the fluid used to fill reservoir 38 and pressure sensing cavity 52 comprises a glycerol water composition. The composition used is substantially nonvolatile and incapable of dissolving elastomeric membrane 50 or elastomeric cover 36. It is also contemplated that silicone oil or a mineral oil might alternatively be used for this fluid, so long as the fluid employed is substantially nonvolatile and does not dissolve or attack the materials used in the pressure monitoring apparatus. In the preferred embodiment, a urethane membrane, type X1405-20, available from Deerfield Urethane Product Company, is used for the elastomeric membranes 46 and 50 and elastomeric cover 36. Alternatively, a latex membrane may be used.

Figure 5:
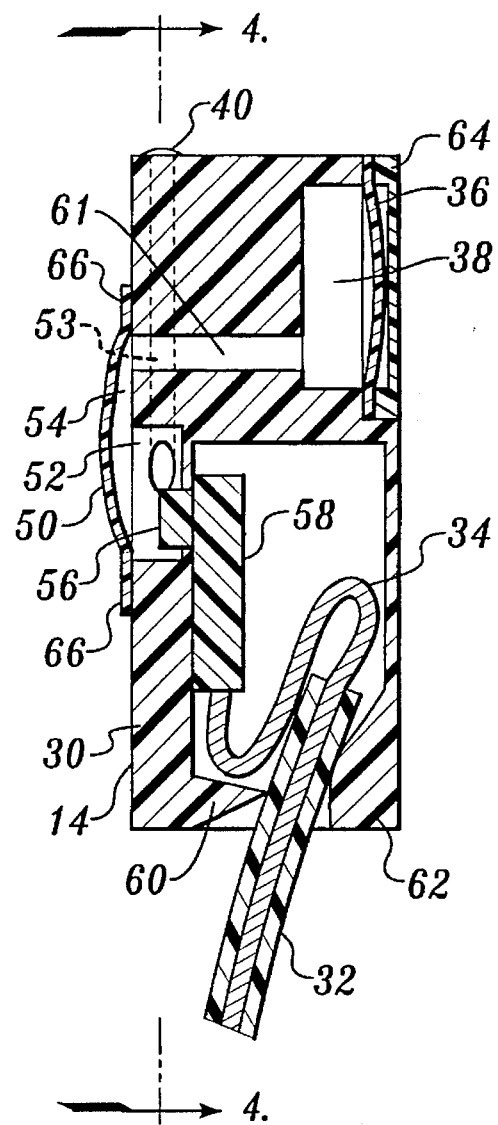
FIG. 5 is a cross-sectional view of the reusable portion of the first embodiment, along section line 5—5 in FIG. 4.

As shown in FIGS. 4 and 5, a pressure transducer 56, which is mounted on a pressure transducer substrate 58, is exposed to fluid pressure within pressure sensing cavity 52. Pressure transducer 56 preferably comprises a piezo resistive bridge, the details of which are generally well known to those of ordinary skill in the art. The range of pressure that can be sensed by pressure transducer 56 in the preferred embodiment is from −30 to +300 millimeters of mercury. Pressure transducer substrate 58 may include other circuitry for scaling and offset adjustment. Conductors 34, which are connected to pressure transducer substrate 58, loop under the pressure transducer chip and into a sensor cable 32. Sensor cable 32 is secured to the reusable housing between a clamp 60 and an opposing cable cover 62.

Figure 6:
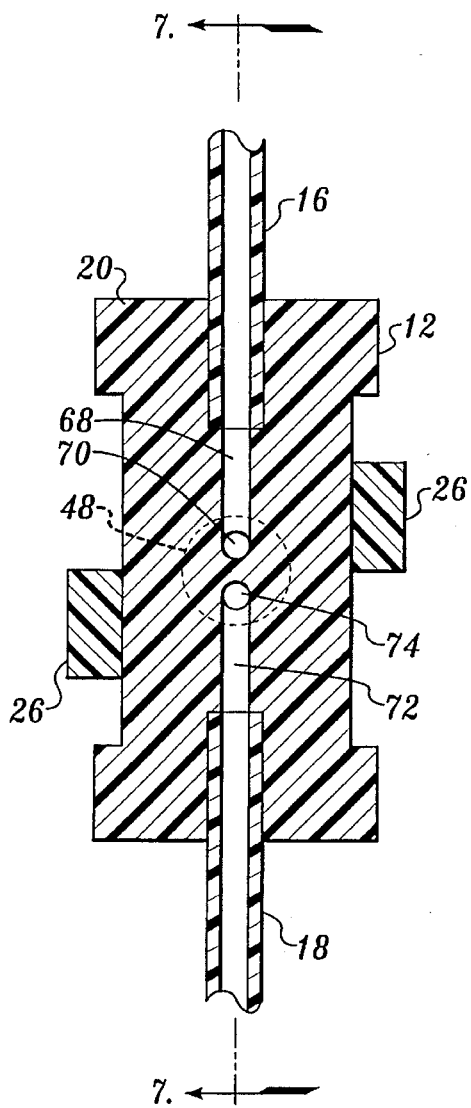
FIG. 6 is a cross-sectional view of the disposable portion of the first embodiment, along section line 6—6 in FIG. 7.
Figure 7:
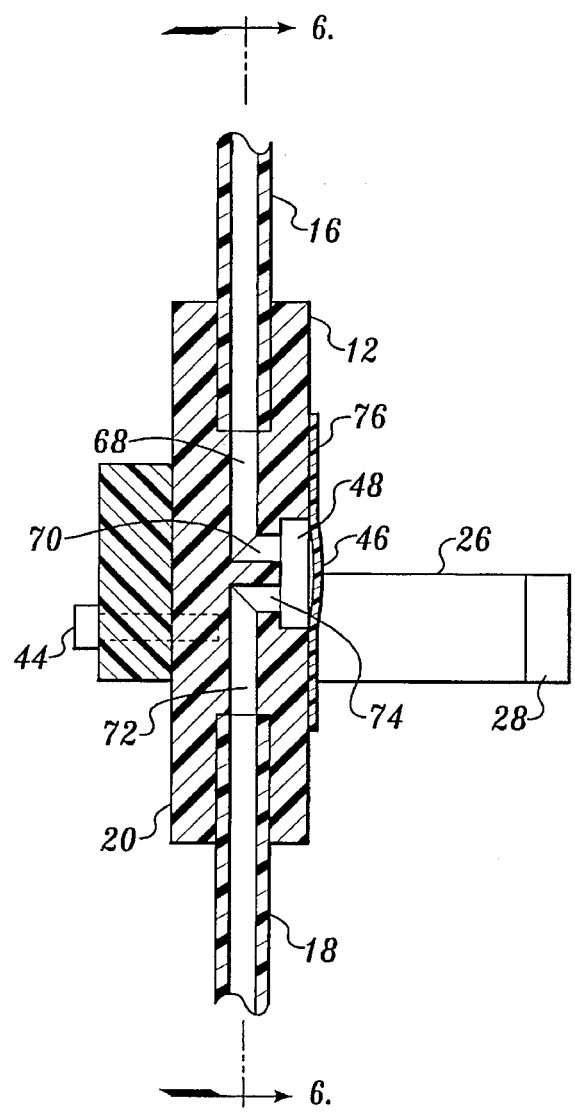
FIG. 7 is a cross-sectional view of the disposable portion of the first embodiment, along section line 7—7 in FIG. 6.

Turning to FIGS. 6 and 7, details of the interior of disposable portion 12 are illustrated in two cross-sectional views. The path followed by the medicinal fluid flowing into the disposable portion through inlet port 16 and out through outlet port 18 is most clearly shown in FIG. 7. The medicinal fluid flowing into the disposable portion travels through an inlet passage 68, which is generally aligned along the longitudinal center of disposable housing 20. The fluid then flows transversely into cavity 48 through a connecting passage 70. From cavity 48, the fluid flows out through a connecting passage 74 and into an outlet passage 72. Outlet passage 72 is connected in fluid communication with outlet port 18. The pressure of the medicinal fluid in cavity 48 acts on elastomeric membrane 46, causing the elastomeric membrane to be slightly distended as a function of the fluid pressure. Since elastomeric membrane 46 is adhesively secured to a peripheral surface 76 of disposable housing 20 around cavity 48, the elastomeric membrane seals the outer opening into cavity 48, and the force of the fluid pressure in cavity 48 is applied over the area of the elastomeric membrane covering the opening into the cavity.

Figure 8:
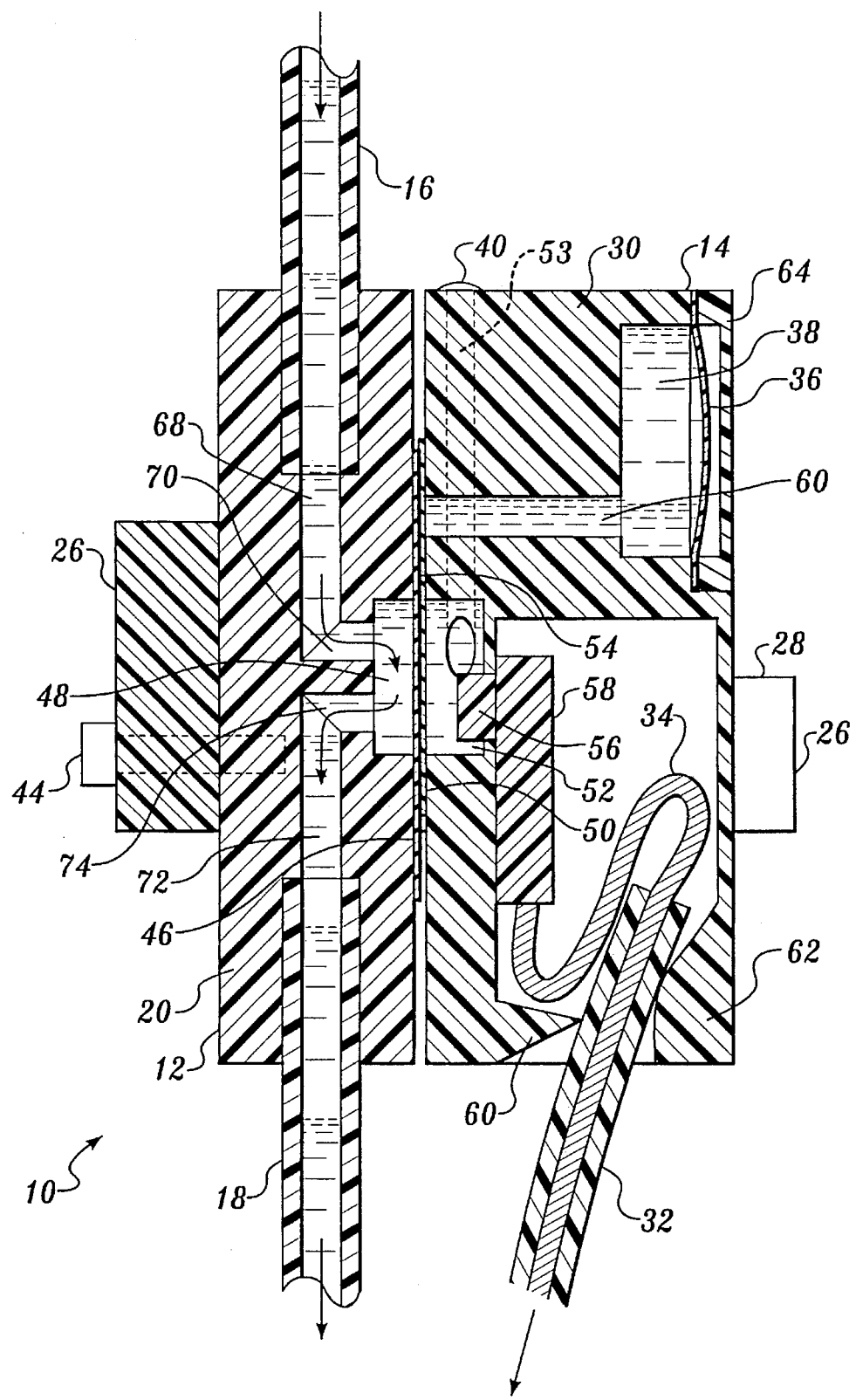
FIG. 8 is a longitudinal sectional view of the pressure monitoring apparatus of FIG. 1.

As shown in FIG. 8, when disposable portion 12 is brought into engagement with reusable portion 14, it is held in place by tangs 28 on retainer clips 26. When the two portions of the pressure monitor are thus engaged, elastomeric membrane 50 on the reusable portion contacts elastomeric membrane 46 on the disposable portion. Elastomeric membrane 46 compresses the portion of elastomeric membrane 50 that defines pressure equalization passage 54 against the underlying surface of reusable housing 30, closing the pressure equalization passage. Closure of fluid pressure equalization passage 54 interrupts fluid communication between reservoir 38 and pressure sensing cavity 52. Because the pressure within pressure sensing cavity 52 is greater than atmospheric pressure, full and intimate contact between elastomeric membrane 50 and elastomeric membrane 46 is assured so that the pressure of the medicinal fluid within cavity 48 of the disposable portion is accurately transmitted between elastomeric membrane 46 and elastomeric membrane 50 and through the fluid within pressure sensing cavity 52, to act on pressure transducer 56.

Since engagement of the disposable portion with the reusable portion interrupts fluid communication between pressure sensing cavity 52 and reservoir 38 through pressure equalization passage 54, the total volume of fluid used to transmit pressure from elastomeric membrane 50 to pressure transducer 56 is minimized, thereby improving the compliance of the pressure monitor. In this manner, the frequency response is increased, to a level exceeding 20 Hz. When blood pressure is monitored with a device having an upper frequency response greater than about 20 Hz, physiological artifacts within the cardiovascular system can more readily be detected.

Since reusable portion 14 never comes into contact with any fluid exposed to a patient's vascular system, it is not contaminated, and can be reused with a different disposable portion, when it is necessary to measure pressure for another patient. Reusable housing 30 and disposable housing 20 are formed of an injection molded plastic and are relatively inexpensive. Disposable portion 12 does not include any electronic components; therefore, its cost is minimized. Conversely, since reusable portion 14 is employed to monitor pressure for a number of patients, pressure transducer 56 (and pressure transducer substrate 58) can be of higher quality and somewhat higher cost than is typically used in conventional fully disposable pressure monitoring apparatus intended to be discarded after use with a single patient.

Figure 10:
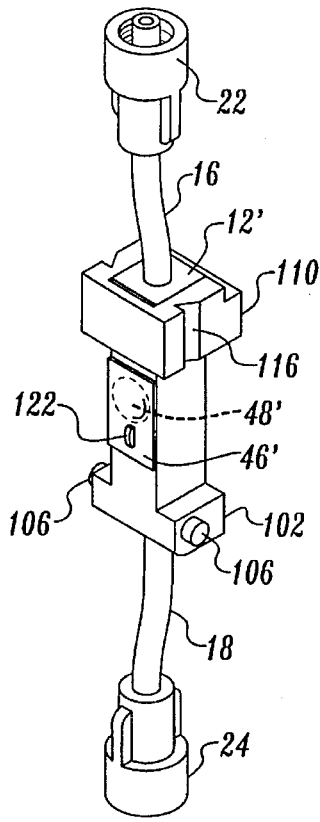
FIG. 10 is an isometric view of the disposable portion of the pressure monitoring apparatus of FIG. 9, showing a surface of the disposable portion that contacts the reusable portion and showing a slider disposed in a position to engage the reusable portion.

FIGS. 9–11 disclose a second embodiment of a pressure monitoring apparatus 100. Pressure monitoring apparatus 100 is similar to pressure monitoring apparatus 10 in most respects, and for this reason, elements of the two embodiments that are identical in form and function are assigned the same reference numbers in the drawings. However, where elements have a common function, but a different form or configuration, in pressure monitoring apparatus 100, these elements are designated using reference numerals that include a prime designation.

For example, a disposable portion 12' in pressure monitoring apparatus 100 has a different configuration than disposable portion 12, but provides the same function, i.e., conveying fluid from a source (not shown), in through inlet port 16 and out through outlet port 18. Reusable portion 12' comprises a reusable portion 14' that is configured differently, but is used for housing pressure transducer 56 to monitor the pressure of fluid flowing through the disposable portion.

One of the more significant differences between pressure monitoring apparatus 10 and pressure monitoring apparatus 100 is in the mechanism used for coupling and engaging disposable portion 12' with reusable portion 14'. Disposable portion 12' includes a disposable housing 102. On opposite sides of the disposable housing, adjacent the end connected to outlet port 18, are disposed projecting nibs 106. A reusable housing 104 includes a pair of forwardly projecting hooks 108, which are sized and configured to engage projecting nibs 106 on the disposable housing. To seat the disposable portion into engagement with the reusable portion, projecting nibs 106 are dropped into hooks 108, and the disposable portion is pivoted into contact with the facing surface of reusable portion 14'.

Captive on disposable portion 12' is a slider 110, which extends like a quadrilateral-shaped ring around disposable housing 102. Slider 110 slides longitudinally along disposable housing 102, between the position in which it is shown in FIGS. 9 and 10 and the position in which it is shown in FIG. 11. When disposable portion 12' is engaged with reusable portion 14', slider 110 is slid to the position shown in FIG. 10 so that tangs 114, which project inwardly from a clip 112 on reusable housing 104, engage corresponding grooves 116 on opposite sides of the slider. Engagement of tangs 114 in grooves 116 locks the disposable portion into intimate contact with the reusable portion. When not engaged with the reusable portion, slider 110 is left in the position shown in FIG. 11, wherein the slider covers elastomeric membrane 46. When slider 110 covers cavity 48', it protects elastomeric membrane 46 from possible damage in the event that fluid at a pressure in excess of the rated pressure for elastomeric membrane 46 is injected through disposable portion 12'. For example, during backflushing operations of disposable portion 46, it is possible that a fluid at pressures in excess of 100 psi may be applied, which could destroy the disposable portion by rupturing elastomeric membrane 46. However, when slider 110 is positioned so as to cover elastomeric membrane 46, the membrane is protected from over extension and damage due to such pressures.

A lower stop 120 limits the travel of slider 110 when it is moved to the position to cover elastomeric membrane 46. An upper stop 118 prevents slider 110 from slipping off disposable housing 102 by limiting its upward travel in the position where it engages tangs 114 on clip 112.

As shown in FIG. 10, immediately below elastomeric membrane 46 is disposed a short ridge or "bump" 122. Ridge 122 is intended to compress elastomeric membrane 50' into a fluid pressure equalization passage 54' that couples pressure sensing cavity 52' in fluid communication with the reservoir 38 within reusable portion 14'. Fluid pressure equalization passage 54' comprises a shallow channel formed in the surface of reusable housing 104. However, ridge 122 forces elastomeric membrane 50' into fluid pressure equalization passage 54', thereby interrupting fluid flow between the reservoir and pressure sensing cavity 52'. This same approach could also be used on pressure monitoring apparatus 10.

Since pressure sensing cavity 52' is also filled with fluid at a pressure in excess of atmospheric pressure (approximately 10 millimeters of mercury), elastomeric membrane 50 is forcibly distended so that it is in substantially full and intimate contact with elastomeric membrane 46, which overlies cavity 48'. Thus, the same features and advantages are provided in pressure monitoring apparatus 100 as in the first embodiment.

Referring now to FIG. 12, a third embodiment for a pressure monitoring apparatus 200 is illustrated. In this embodiment, a disposable housing 202 includes ridges 220 along each side, for engaging lips 222 that are formed on each side of a reusable housing 204. As was the case in the previous embodiment, the same reference numerals are used for those elements that are generally identical in form and function to those in the first embodiment. However, pressure monitoring apparatus 200 differs in two significant respects from the first two embodiments. Specifically, it does not include a clip for holding the disposable portion in engagement with the reusable portion during the monitoring of pressure for a fluid flowing through inlet port 16 and out outlet port 18; and, it does not use elastomeric membrane 50 as a valve. Instead of a clip, pressure monitoring apparatus 200 includes a rotatable clamp/valve 206. The rotatable clamp/valve includes a shaft 208 that extends through reusable housing 204 and into reservoir 38. A retainer ring 210 secures shaft 208, preventing the shaft from pulling from reusable housing 204. At about its midpoint, shaft 208 passes through fluid injection passage 53', which is coupled in fluid communication with reservoir 38 through a transverse passage 207. Shaft 208 includes a valve passage 214, which is oriented in an open position when reusable portion 14" is not engaged with disposable portion 12". In this position, reservoir 38 is in fluid communication with pressure sensing cavity 52. Clamp/valve 206 includes a handle 212 that facilitates rotation of shaft 208 around its longitudinal axis. Rotation of shaft 208 through an angle of about 90° in this manner interrupts fluid communication through fluid injection passage 53' and brings a helical clamp thread 216 disposed circumferentially around shaft 208 into engagement against a projecting lip 218 on disposable portion 12". Helical clamp thread 216 exerts an increasing pressure against projecting lip 218, to lock disposable portion 12" against reusable portion 14" as shaft 208 is rotated. When the disposable portion is thus engaged with the reusable portion, fluid pressure in cavity 48 is transmitted through an elastomeric membrane 46', which sealingly encloses cavity 48, and through elastomeric membrane 50 to the fluid within pressure sensing cavity 52. This fluid conveys the pressure to pressure transducer 56. Fluid within pressure sensing cavity 52 is at a pressure approximately 10 millimeters of mercury (in excess of atmospheric pressure) to ensure that elastomeric membrane 50 is partially distended and is substantially in full and intimate contact with elastomeric membrane 46. When fluid communication between reservoir 38 and the pressure sensing cavity is interrupted as shaft 208 is rotated to lock the disposable portion into engagement with the reusable portion, the limited volume of fluid (in pressure sensing cavity 48) that is exposed to the pressure transmitted between the elastomeric membranes ensures that the required high frequency response (>20 Hz) for pressure monitoring apparatus 200 is achieved.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A pressure monitor for monitoring fluid pressure in a line that is in fluid communication with a physiological fluid, comprising:

a) a disposable portion that includes a first housing, said disposable portion further comprising:

(i) a port adapted to couple to said line;
(ii) a first cavity disposed in said first housing, in fluid communication with the port; and
(iii) a first elastomeric membrane sealingly covering said first cavity;

(b) a reusable portion that includes a second housing adapted to engage and couple with said first housing, said reusable portion comprising:

(i) a second cavity disposed in said second housing;
(ii) a second elastomeric membrane covering said second cavity and disposed to contact said first elastomeric membrane when the first housing is engaged with the second housing; and
(iii) a reservoir disposed in said second housing, in fluid communication with said second cavity via a passage that connects the reservoir to the second cavity when the first housing is not engaged with the second housing, said reservoir, said passage, and said second cavity being filled with a substantially nonvolatile fluid; and (c) a pressure transducer disposed adjacent to said second cavity, for producing a signal indicative of the pressure of the fluid in the line when the first housing is engaged with the second housing, engagement of said first housing with said second housing interrupting the fluid communication through the passage between the reservoir and the second cavity to minimize the volume of the nonvolatile fluid that transmits pressure from the second membrane to the pressure transducer, so that a characteristic maximum frequency response of the pressure monitor is substantially higher than it would be if the fluid communication through the passage were not interrupted.

2. The pressure monitor of claim 1, wherein the second elastomeric membrane defines one side of the passage, said elastomeric membrane elastically distending away from an underlying surface of the second housing to enable the nonvolatile fluid to flow between the second elastomeric membrane and the underlying surface of the second housing in fluid communication between the reservoir and the second cavity.

3. The pressure monitor of claim 2, wherein a surface of the first housing that abuts against a corresponding surface of the second housing includes a ridge that extends outwardly to force the second elastomeric membrane into the passage and thereby interrupt fluid communication between the reservoir and the second cavity when the first housing is engaged with the second housing.

4. The pressure monitor of claim 1, further comprising a valve that interrupts fluid communication between the reservoir and the second cavity when the first housing is engaged with the second housing.

5. The pressure monitor of claim 1, wherein the nonvolatile fluid is pressurized to a pressure in excess of ambient air pressure, thereby causing the second elastomeric membrane to distend outwardly, ensuring a substantially full contact between the first elastomeric membrane and the second elastomeric membrane over the first and the second cavities.

6. The pressure monitor of claim 1, further comprising at least one arm extending from one of the first housing and the second housing and having a tang to engage the other of the first housing and the second housing, said at least one arm and tang holding the first housing in contact and engagement with the second housing when fluid pressure in the line is being monitored.

7. The pressure monitor of claim 1, further comprising a protective cover for the first elastomeric membrane that is used to cover the first cavity when the first housing is not engaged with the second housing, to prevent a potentially damaging distention of the first elastomeric membrane that might be caused by an excessive fluid pressure in the first cavity.

8. The pressure monitor of claim 7, wherein the protective cover comprises a slide that is movable between a first position, in which the slide covers the first elastomeric membrane, and a second position, in which the slide engages the second housing to hold the first housing against the second housing, with the first elastomeric membrane in contact with the second elastomeric membrane.

9. A disposable device for use in monitoring fluid pressure, comprising:
   (a) a housing having an inlet port adapted to couple to a source of a medicinal fluid, and an outlet port adapted to connect in fluid communication with a patient's body;
   (b) a chamber formed in said housing, said chamber being in fluid communication with both the inlet port and the outlet port;
   (c) an elastomeric membrane that sealingly covers said chamber, defining a side of the chamber; and
   (d) a ridge formed on a surface of the housing, adjacent to the chamber and the elastomeric membrane, said ridge extending outwardly from the surface and thereby adapted to interrupt a fluid communication through a passage within a reusable pressure transducer when the disposable device is mated with the reusable pressure transducer for monitoring the pressure of the physiological fluid.

10. The disposable device of claim 9, further comprising a plurality of arms extending on opposite sides of the housing, each of said arms including a tang that is adapted to engage the pressure transducer, holding the housing in a predefined position relative to the pressure transducer, to enable the pressure of physiological fluid to be monitored thereby.

11. A method for monitoring a physiological fluid pressure that enables a pressure transducer employed to monitor the physiological fluid pressure to be used in monitoring the physiological fluid pressure of other patients without cross contamination between patients, comprising the steps of:
   (a) administering a medicinal fluid to a patient through a disposable device that includes a pressure chamber covered by a first elastomeric diaphragm, said medicinal fluid flowing through the pressure chamber so that the first elastomeric diaphragm is exposed to medicinal fluid;
   (b) providing a reusable pressure monitoring device, said reusable pressure monitoring device including a second elastomeric diaphragm covering a cavity filled with a substantially nonvolatile fluid, said nonvolatile fluid being provided from a reservoir in the reusable pressure monitoring device and transmitting pressure from the second elastomeric membrane to a pressure transducer in the reusable pressure monitoring device;
   (c) coupling the disposable device to the reusable pressure monitoring device, so that the first elastomeric membrane contacts the second elastomeric membrane; and
   (d) interrupting fluid communication between the reservoir and the cavity when the disposable device is coupled to the reusable pressure monitoring device, to increase a frequency response of the reusable pressure monitoring device.

12. The method of claim 11, wherein the step of interrupting the fluid communication between the reservoir and the cavity comprises the step of blocking a fluid passage disposed between the reservoir and the cavity.

13. The method of claim 11, wherein the disposable device depresses the second elastomeric membrane to interrupt the fluid communication between the reservoir and the cavity.

14. The method of claim 11, wherein the step of interrupting the fluid communication between the reservoir and the cavity comprises the step of actuating a valve disposed in a fluid path between the reservoir and cavity.

15. The method of claim 11, further comprising the step of covering the first elastomeric membrane when the disposable device is not mated to the reusable pressure monitoring device, in order to prevent a damaging distention of the first elastomeric membrane if the pressure of a fluid in the pressure chamber exceeds a rated limit.

16. The method of claim 15, further comprising the step of using a slide to cover the first elastomeric membrane, and moving the slide from a position in which the slide covers the elastomeric membrane to a different position in which the slide engages the reusable pressure monitoring device in order to hold the disposable device in contact with the reusable pressure monitoring device.

17. The method of claim 11, further comprising the step of pressurizing the nonvolatile fluid to a pressure in excess of ambient air pressure, so that the second elastomeric membrane is distended sufficiently to more effectively contact the first elastomeric membrane.

* * * * *

UNITED STATES PATENT AND TRADEMARK OFFICE
CERTIFICATE OF CORRECTION

PATENT NO. : 5,551,300
DATED : September 3, 1996
INVENTOR(S) : Gerald G. Vurek et al.

It is certified that error appears in the above-indentified patent and that said Letters Patent is hereby corrected as shown below:

Item [57], Abstract, Line 14     "reservoir(38)" should read --reservoir (38)--

Column 1, Line 57     "robber" should read --rubber--

Column 5, Line 15     "or" should read --of--

Column 10, Line 42 (Claim 3)     "claim 2" should read --claim 1--

Column 11, Line 13 (Claim 9)     after "monitoring" insert --a physiological--

Signed and Sealed this

Twenty-fifth Day of March, 1997

Attest:

BRUCE LEHMAN

*Attesting Officer*     *Commissioner of Patents and Trademarks*